United States Patent [19]
Larsson

[11] Patent Number: 6,037,171
[45] Date of Patent: Mar. 14, 2000

[54] CELL CULTURE MICROCHAMBERS IN A GRID MATRIX SANDWICHED BETWEEN A PLANAR BASE AND SEMIPERMEABLE MEMBRANE

[75] Inventor: Börg Larsson, Zurich, Switzerland

[73] Assignee: Microcloning CCCD AB, Jonkoping, Sweden

[21] Appl. No.: 09/051,314

[22] PCT Filed: Sep. 25, 1996

[86] PCT No.: PCT/CH96/00332

§ 371 Date: May 4, 1998

§ 102(e) Date: May 4, 1998

[87] PCT Pub. No.: WO97/13839

PCT Pub. Date: Apr. 17, 1997

[30] Foreign Application Priority Data

Oct. 6, 1995 [CH] Switzerland ............................ 2827/95

[51] Int. Cl.[7] .............................. C12M 3/00; C12N 5/00; C12N 11/00; C12N 11/14
[52] U.S. Cl. ....................... 435/297.1; 435/174; 435/176; 435/180; 435/383; 435/395; 435/401; 435/289.1; 435/305.2; 435/305.3
[58] Field of Search ..................... 435/174, 176, 435/180, 289.1, 297.1, 305.2, 383, 395, 401, 305.3

[56] References Cited

U.S. PATENT DOCUMENTS

| | | | |
|---|---|---|---|
| 4,514,499 | 4/1985 | Noll | 435/240 |
| 4,693,983 | 9/1987 | Davies et al. | 435/284 |
| 5,726,060 | 3/1998 | Bridges | 435/240.241 |

FOREIGN PATENT DOCUMENTS

| | | |
|---|---|---|
| 014007 | 8/1980 | European Pat. Off. . |
| 2693739 | 1/1994 | France . |
| 9527196 | 10/1995 | WIPO . |

*Primary Examiner*—David M. Naff
*Attorney, Agent, or Firm*—Notaro & Michalos P.C.

[57] ABSTRACT

A compact arrangement for cell culture is provided by sandwiching a grid matrix containing a multiplicity of perforations therethrough between a planar base and a semipermeable membrane such that the perforations define microchambers for cell culture. The perforations may be in a regular patten such as a honeycomb pattern, and be circular to form microchambers having a diameter of approximately 0.2 to 5 mm. A magnet means can be used to hold the sandwich structure together by placing a magnet on a side of the base opposite the grid matrix and a magnetically attractable film on a side of the membrane opposite the grid matrix. The base may have a diameter of approximately 5 to 20 cm, and be coated with a layer such as an agarose layer lacking cell affinity. A spot surface that forms an island having cell affinity is placed on the layer centrally within each perforation. The arrangement allows independent and simultaneous culture of multiple biological samples, and permits microscopic or spectroscopic analysis of the microchambers.

17 Claims, 9 Drawing Sheets

6,037,171

CELL CULTURE MICROCHAMBERS IN A GRID MATRIX SANDWICHED BETWEEN A PLANAR BASE AND SEMIPERMEABLE MEMBRANE

FIELD AND BACKGROUND OF THE INVENTION

The present invention relates to an arrangement of habitats, separated from one another, of microscopic dimensions, a method for producing such arrangement as well as methods for investigations and measurements with the aid of this arrangement.

The arrangement described in the present invention of habitats of microscopic dimensions, laid out with microscopic precision on a planar support and separated from one another, is especially suited for the aseptic culture and observation of single cells and their monoclonal descendants as well as also for the culture and study of other small colonies such as bacteria, human, animal or plant cell populations, tissue cultures, mammalian or plant embryos, insects or nematodes at different developmental stages.

To do so, the cells or the other biological samples cited above are placed individually or in relevant combinations into a "pond" disposed on a flat, precisely prepared base; for example a semiconductor, quartz, glass, synthetic or metal base, and covered with a thin semipermeable sheeting, which pond is thin and of extremely small dimensions and which thus forms a sterile microlaboratory. Into each such pond which forms a boxlike closable microchamber, concentrations, adapted to the particular emplaced culture, are added of, for example, buffer components, oxygen, nutrient substances, protective antibiotics, active substances such as pharmacological agents, analytically useful reagents such as for example fluorescent coloring agents etc, by means of penetration of culture media through the semipermeable closable cover sheeting. The supply of, for example, growth factors or other macromolecular medium-specific substances, depending on the selected pore size of the sheeting, can be ensured either before or after the closing of the chamber respectively the pond. It is therein advantageous, for example to place patient sera and expensive biomolecule-preparations into the ponds before closing it in order to minimize its use and to be able to control the concentration in the chambers individually.

The described arrangement provides good conditions for the individual handling and the microscopic observation of the cultures generated therein with respect to their individual properties for example for the controlled exposition in the presence of physical, chemical or other agents and for the optical and physicochemical monitoring and characterization as well as for the final intravital or postmortal storage. This storage can take place for example through deep-freezing or after chemical fixing.

In genetics, microbiology, immunology, oncology, radiobiology, pharmacology, embryology, zoology and botany the need exists for the individual culture of individual cells or multicell samples, in order to observe the growth and the properties of the cultures developing therein, to document them or to preserve them alone or fixed. The invention therefore comprises, in addition to the cited arrangement, respectively its preparation, further the adaptation of the described structures and corresponding measuring parameters in view of embedding the new technology in the current biomedical and biotechnical research and development, as well as for the needs of the intended important applications in clinical diagnostic and therapeutic planning, for the so-called "gene-technology engineering" and applied toxicology or environmental hygiene or pharmacology.

Because the cover sheeting of the ponds can be impermeable to bacteria, viruses and other biological contaminants the microchambers present can be used as sterile laboratories for biological cells. A problem presents itself in the exchange of nutrients and other substances which is only limited via the cover sheeting. With the suggested construction and the tiny cell mass of the individual cultures this exchange problem can, however, be eliminated or reduced.

SUMMARY OF THE INVENTION

It is a task of the present invention to create an arrangement by means of which, to the highest extent independently and simultaneously a multiplicity of biological samples can be cultured and simultaneously be observed in an extremely simple manner. In the case of monoclonal cell populations chamber-like microlaboratories are created which permit especially favorable conditions for culture and analysis. Therewith, for example in the presence of genetic uniformity, the advantage is attained that from a tumor sample comprising a few hundred thousand or million cells, the reliable characterization of a representative selection of cloned cells is made possible. By creating discrete, separate, individual places for at least approximately 1000 clones the task according to the invention ought to, for example, be solved in clinical oncology by creating the preconditions for the desired representativeness of the cited selection. It is understood that it should also be possible to apply the arrangement for the culture, study and storage of smaller quantities of cell populations down to a single cell in a miniature laboratory.

Further tasks comprise being able to provide the arrangement in extremely simple manner with the individual cells and, during the culture and observation of the growth and the cell properties, to eliminate any undesired external influences on the uniformity of the growth conditions in the microchambers respectively in the discrete "ponds".

A further task, on the other hand, comprises creating suitable measuring methods in order to record or evaluate the arrangements created according to the invention respectively the cells or biological cultures disposed therein during the growth phase.

The tasks posed according to the invention are solved in particular by means of an arrangement according to the formulation of the claims.

According to the invention an arrangement for culturing cells is proposed which comprises a multiplicity of microchambers or "ponds" which are separated from one another and are disposed with microscopic precision for example in the form of honeycombs on a disk-like planar base. The microchambers are covered by a semipermeable wall or sheeting, i.e. against biological contaminations of the environment. The chamber structure is typically a so-called sandwich structure of parallel planar thin plates and/or in combinations selected for different application purposes. Plates or films disposed centrally in the sandwich structure are implemented such that they are perforated in partially net-like or honeycomb-like manner for the formation of the microchambers. The base which can also be part of the "sandwich structure" is for example a disk formed by a thin silicon, quartz, glass or synthetic material structure. Depending on the number and size of the microchambers to be disposed on the base, the surface diameter of the base can be 5 to 20 cm. With the selection of a circular base a possible embodiment variant of the arrangement is attained which can best be compared to a compact disk used in the audio and video field, and which can be scanned by means of, for example, microscopic or spectroscopic analysis of the microchambers.

The microchambers, disposed for example in the form of honeycombs, can typically, however not necessarily, be implemented circularly with a diameter of approximately 0.5 to 5 mm. Between the honeycomb structure defining the chamber geometry, which also determines the distribution, form and size of the chambers, and the disk-like base can, if advantageous, be disposed a thin transparent film or a thin layer of a transparent gel lacking any cell affinity, such as, for example, an agarose layer. It is understood that for the formation of this layer another suitable material can be used which is extremely inert with respect to cells or their cultures or has other properties.

On the bottom of each microchamber of the honeycomb structure or resting on the base or on the cited film or gel layer can be arranged a typically concentrically implemented surface with cell affinity, comprising a thin metal or molecule layer suitable for the culture of cells and having cell affinity, such as for example a concentrically implemented "palladium island", or comprising another surface-forming material with identical function. The honeycomb structure itself or the chamber walls can be fabricated of a dimensionally stable material, such as for example synthetic material, metal, ceramic or a composite material. The semipermeable membrane, lastly, comprises advantageously a material, at least nearly transparent to light, such as Teflon, polycarbonate or polystyrene.

Further preferred embodiment variants of the arrangement and process according to the invention for the production of the arrangements for culturing cells are also disclosed.

The individual process steps for the production of the arrangement according to the invention will be described in further detail with reference to the Figures described in the following.

The present invention or arrangement, also referred to as Compact Cell Culture Disk (CCCD) permits the microscopic, molecular biological, biochemical and physicochemical studies of individual cells or cell or multicell structures, in small as well as in large number, i.e. from a single cell to typically a few 1000 cells under physically, chemically or biologically optimized conditions. Implanted into the suggested cell culture arrangement together with biological materials a microlaboratory is created which permits the control, observation and analysis of the individual cultures or their formation, with the control of the environment being possible separately or in toto. The entire arrangement as well as also the individual chambers, or miniature microlaboratories can be kept under sterile or nonsterile conditions for short periods of time as well as also for long periods of time as well as also for permanent storage, transport or for observation purposes, for example under a microscope or with spectroscopic methods, for example by utilizing fiber-optic waveguides, photomultipliers or photodiodes.

Lastly, a process is suggested for measuring or recording, evaluating and potentially for storing information regarding the cells or cell culture clones implanted or deposited in the arrangement, defined according to the invention, and other above listed biosamples. These are preferably automatic, electronic data processing-supported processes which can increase the implantation and analysis capacity as well as the speed, in connection with manual and visual techniques.

BRIEF DESCRIPTION OF THE DRAWINGS

The invention will now be described in further detail by example and with reference to the enclosed Figures. Therein depict.

DESCRIPTION OF THE PREFERRED EMBODIMENT

Figure 1:
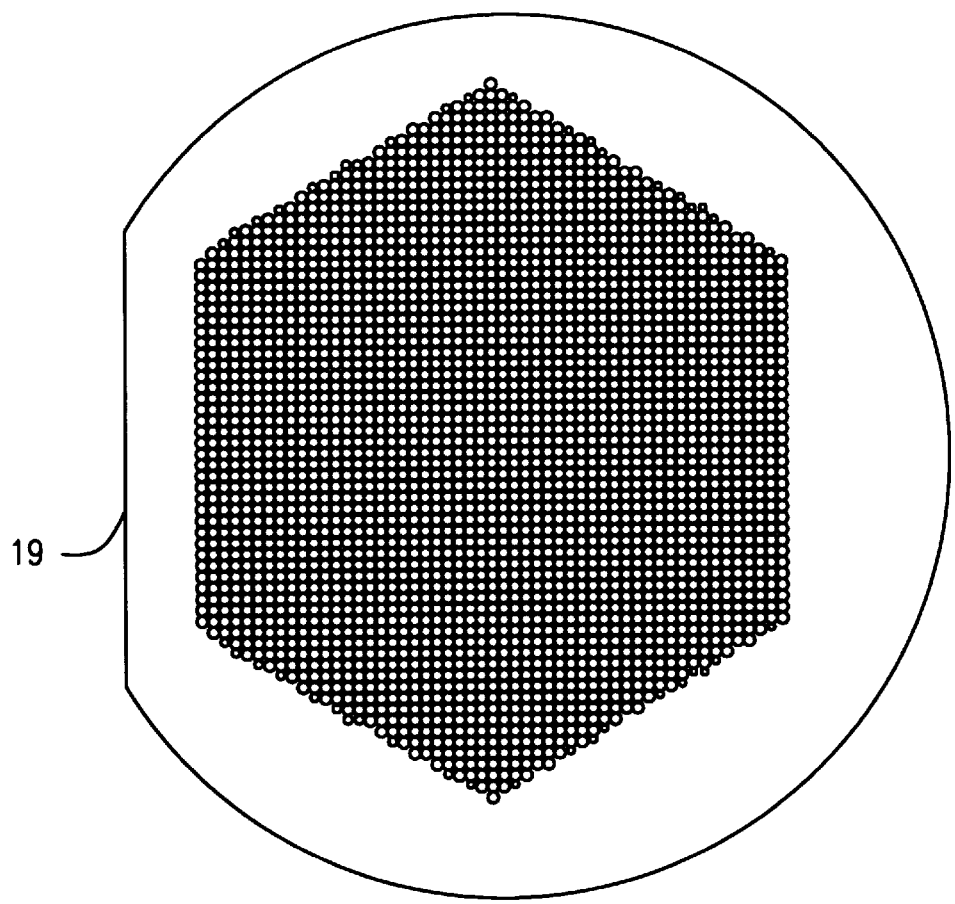
FIG. 1 an example of a disk-like arrangement according to the invention in top view, FIGS. 1a, and b enlarged detail from the arrangement of FIG. 1, FIG. 2 schematically and enlarged different, typically used, individual elements or components of a sandwich-like arrangement according to the invention in cross section, FIG. 2a in cross section a possible embodiment variant of an arrangement in the assembled state as well as in exploded representation, FIG. 2b a further embodiment variant of an arrangement according to the invention in cross section assembled as well as in exploded representation, FIG. 2c again a further possible embodiment variant of an arrangement according to the invention in cross section, assembled as well as in exploded representation, FIG. 3a depicted schematically, a possible in situ measuring method applied to an arrangement according to the invention in cross section, FIG. 3b depicted schematically, a further measuring method of killed material and with covered arrangement in cross section, FIG. 4a depicted schematically in cross section, an embodiment variant of the arrangement according to the invention, FIG. 4b depicted schematically in cross section, a further embodiment variant of an arrangement according to the invention held together by magnetic fields, FIG. 5a depicted schematically in top view a disk-like circularly implemented arrangement according to the invention, FIG. 5b a further embodiment variant in top view implemented analogously to a compact disk, and FIG. 6 depicted schematically in perspective a possible application of the arrangement according to the invention for investigating the biological effectiveness of various types of radiation into an exposed body as a function of the coordinates in a sample system.
Figure 1A:
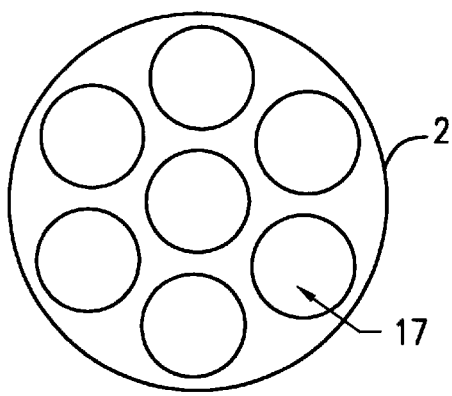
Figure 1B:
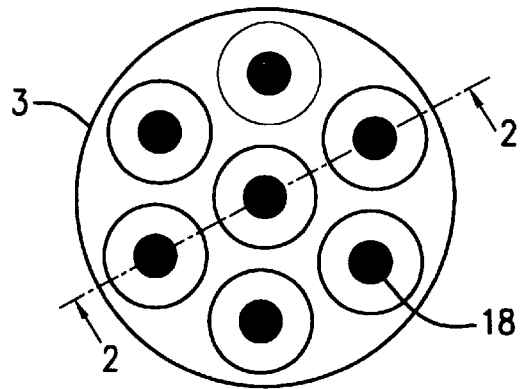

FIG. 1 shows in top view an example of a "compact cell culture disk", or cell culture plate with microchambers in two embodiment variants shown in FIGS. 1a and 1b. The structure of this disk 1 will be explained in further detail with reference to the succeeding FIGS. 2 and following. In the center region of the disk 1 are disposed the microchambers or microlaboratories 17 or 18, defined according to the invention, each comprising a so-called pond closable toward the outside, and in each microchamber or in each pond can be arranged centrally a cell or a cell culture to be cultured. For reasons of manufacturing technology the disk 1 lastly comprises in the margin region a recess or notch 19, the purpose of which is also evident in the following description.

The arrangement of the microchambers 17 depicted in FIG. 1 represents only an example and it is understood that it is possible to arrange the microchambers in any other desired manner on disk 1 as will become evident from the FIGS. 5a and 5b described in the following.

In the two FIGS. 1a and 1b in a detail of disk 1 of FIG. 1 are shown a number of microchambers 17 and in the microchambers in FIG. 1b surfaces 18 are provided in the center having cell affinity, which are absent in the microchambers according to FIG. 1a. Such surfaces of different type, location and implementation and at different positions or other cell-affinitive structures, such as free flowing particles, can also be used.

Figure 2:
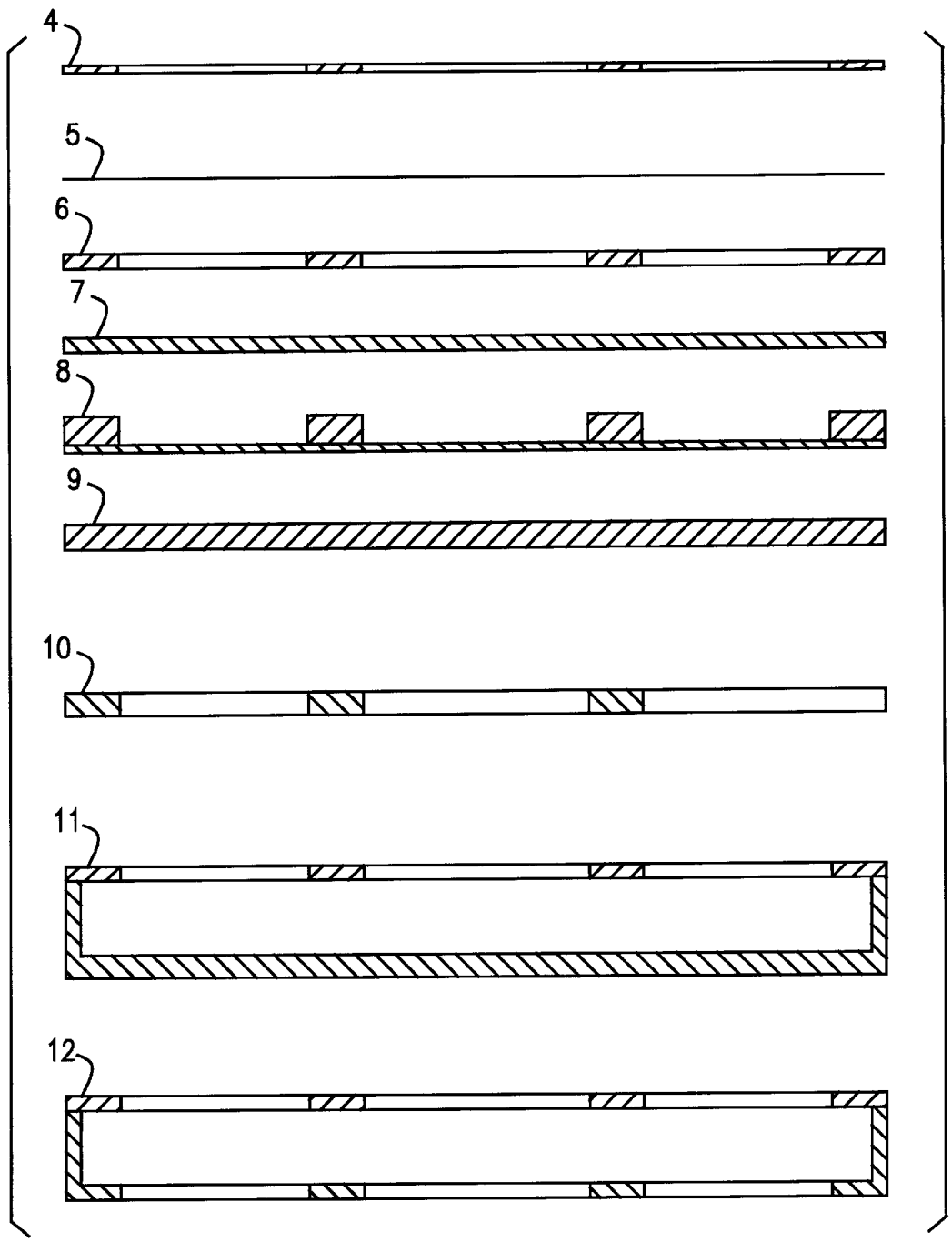

With reference to FIG. 2 as well as 2a to 2c different embodiment variants of possible arrangements according to the invention are shown in cross section with FIG. 2 showing schematically the components or individual elements designated for the structure of the described arrangements. For the structure of the arrangements are to be provided, as shown in FIG. 2, a metal, ceramic or synthetic material sheeting, implemented for example to be perforated honeycomb-like or hole-like, as well as a semipermeable wall 5 which can comprise for example Teflon, polystyrene or any other suitable material preferably transparent to light. For the formation of the microchambers or microlaboratories proper a grid-like or honeycomb-like matrix 6 is used, which is formed of a dimensionally stable material such as for example synthetic material, metal, ceramic or a composite material or reinforced duromers. But this matrix can also be fabricated of a silicon disk treated by means of oxidation or etching, such as denoted in FIG. 2 by the reference number 8. In this case the oxidized or etched silicon matrix is preferably arranged with a transparent quartz layer.

As base for the matrix 6 can be used for example a silicon disk 7 which is provided with cell-affinitive surfaces 18 on which the cells to be cultured can be disposed. This base can, in turn, be part of a silicon disk which is treated by means of oxidation and etching, as, for example, the disk in FIG. 2 denoted by 8 already mentioned above. But this base 7 can, instead of from silicon, also be produced of quartz or glass or of another suitable material. This silicon base is preferably covered with a thin agarose polymer layer, resting on which agarose layer the cell-affinitive spots 18 are disposed, comprising, for example, palladium. In contrast to palladium, agarose does not have any cell affinity. The cited palladium spots are in particular suitable for the culture and cloning of individual cells. The so-called palladium island technique will not be further discussed here since it is well known within relevant prior art for the optimum culture of individual cells. Reference is only made to the literature site: U. Amaldi, B. Larsson, Hadrontherapy in Oncology, Proceedings of the First International Symposium on Hadrontherapy, Como, Italy, Oct. 18–21, 1993, Excerpta Medica, International Congress Series 1077, 1994, Elsevier, pp. 735. It is understood that other similar processes can also be used for this purpose.

Depending on the arrangement selected it is possible to hold the sandwich structure together magnetically, which is the reason for providing a magnet disk 9. This magnet disk can, as denoted by reference symbol 9, be flat or perforated in the form of a honeycomb or hole, as indicated at 10. The latter magnet disk is necessary if, for example, through this magnet disk optical analyses are being performed.

For the secure storing, handling and subsequent transport of the sandwich-like arrangement or analysis structure according to the invention, a container 11 is provided which, for example, can be a special steel box with observation windows provided on at least one side.

Figure 2A:
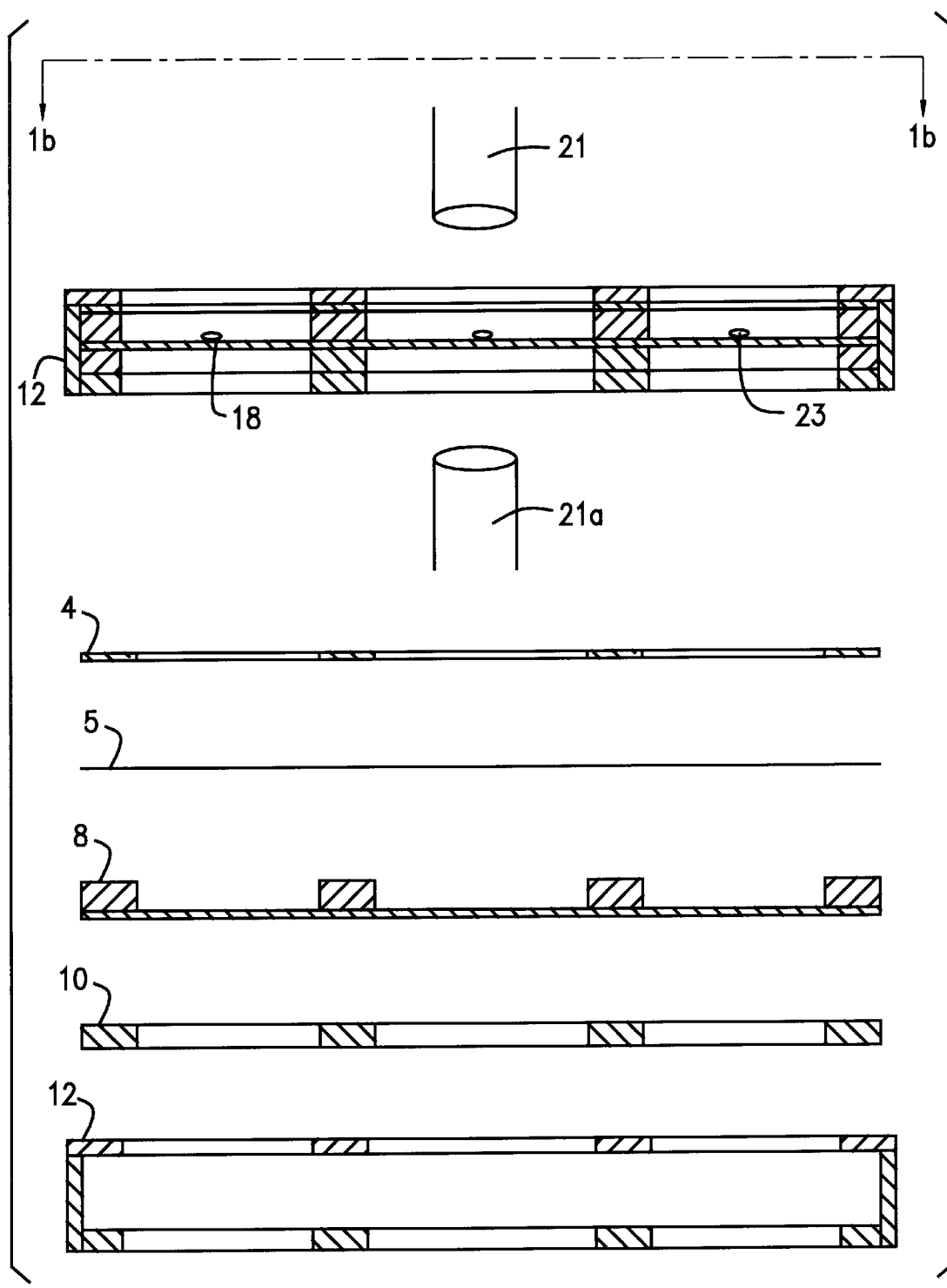

In FIG. 2a a container 11, comprising an arrangement 12, is shown in cross section. For better understanding, the arrangement 12 is shown in exploded view, which clearly shows the individual components used from FIG. 2. The structure or arrangement 12 in FIG. 2a corresponds to the section along line 1b—1b, from FIG. 1b, line 2—2 of FIG. 2a.

The structure or arrangement 12 comprises primarily a silicon disk in the manner of a honeycomb or perforated, which can be combined with a quartz sheeting or quartz disk 8. The perforated openings of the silicon disk 8 can be obtained through oxidation or etching from a silicon disk. The quartz surface is preferably covered with an agarose polymer layer which material does not have any affinity for cells. The structure according to FIG. 2a comprises further a membrane 5 covering the honeycombs as well as a nickel foil 4 implemented in the form of a honeycomb, wherein the honeycomb structure is congruent with that of the silicon disk 8. In order to hold together the structure or arrangement according to the invention, opposite to the silicon honeycomb on the quartz layer a magnet disk 10 is disposed which, again, is provided with corresponding openings congruent with the silicon honeycomb, Through the arrangement of the metal foil and the magnet disk the arrangement is held together by magnetic forces. For the secure storing, lastly, the arrangement 12 is inserted into a container 11, for example comprising special steel, and stored therein. This special steel box can be provided on one side or both sides with window-like openings which, again, are congruent with the silicon honeycomb structure. These window-like openings serve for the purpose of being able to analyze or observe the arrangement or structure or the cells or cell cultures disposed therein through suitable analytical instruments 21 or 21a. As shown in particular through the assembled structure as example of a cell-affinitive structure, the discrete chambers comprise on the quartz surface in the center a palladium island 18.

On this palladium island can adhere a single cell 23 whereupon the culture of the cell commences. The discrete chambers are mixed with various liquids, such as sera, nutrient substances, active agents, etc. Since the structure is covered or closed by means of the semipermeable wall 5, it is possible to add further substances to the chambers during the culture process. This semipermeable wall comprises for example Teflon, polystyrene or another suitable transparent material.

In FIG. 2b again, assembled as well as also in exploded view, a further arrangement according to the invention is shown schematically in cross section and in detail. Again, the detail corresponds approximately to section 1b—1b from FIG. 1b (line 2—2 of FIG. 2b), however, in FIG. 2b no cells are placed into the structure. In the arrangement or structure according to FIG. 2b onto a silicon disk 7 a matrix 6 is placed comprising, for example, polycarbonate. Again, the matrix is covered by a membrane 5, and the entire arrangement is held together by means of magnetic forces through a metal foil and magnet disk. For the storage of the arrangement again a container 11 is provided, however, in the example according to FIG. 2b, the analytical instruments are provided from above through the cover of the container 11 by means of, for example, a measuring device 21. In the present example it is advantageous if, again, the silicon disk is provided by means with an agarose layer. Again, on the agarose layer are provided palladium islands 18 for emplacing the corresponding cells.

Figure 2B:
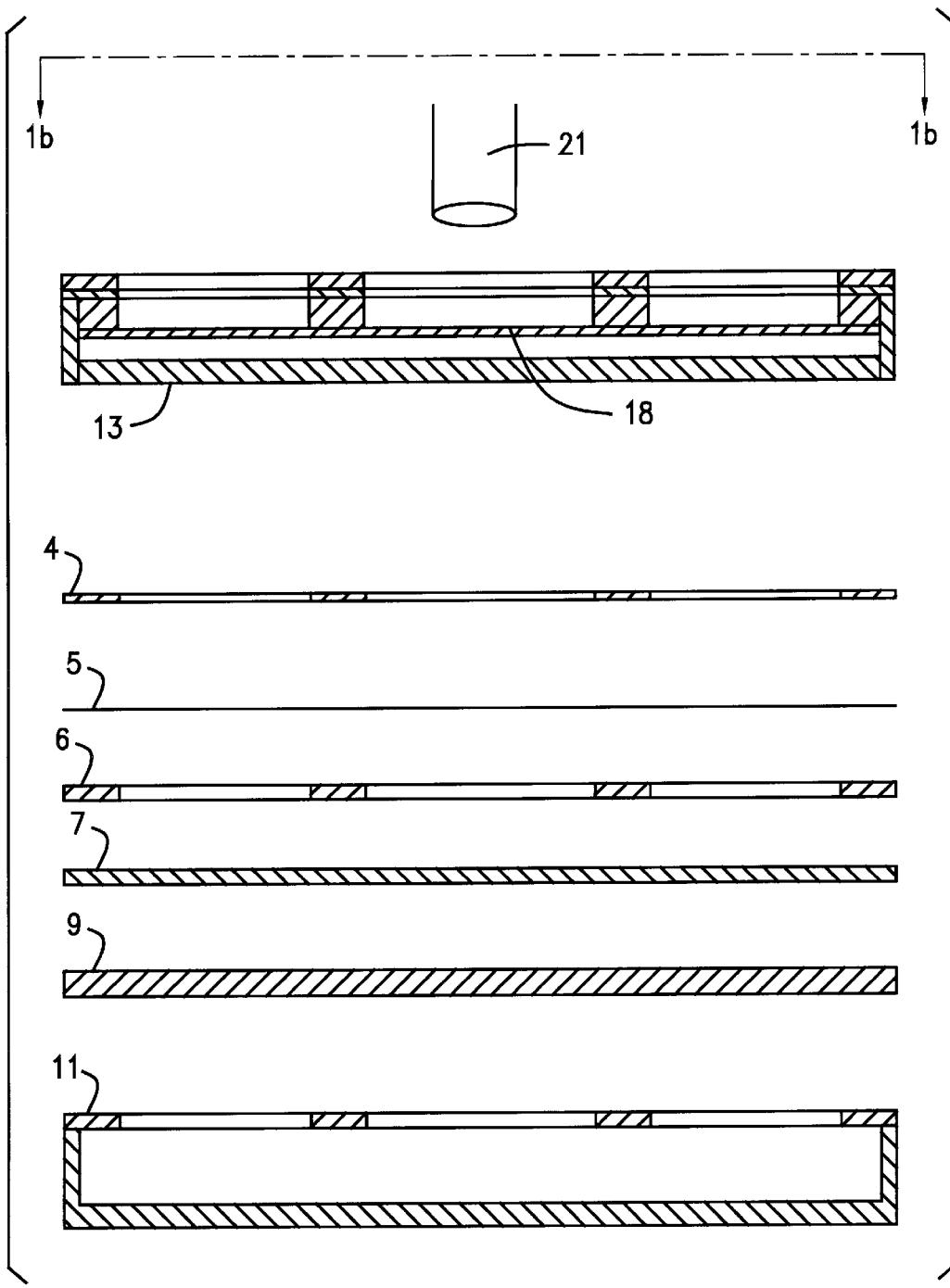

It is understood that it is possible, in the case of structure 12 according to FIG. 2a as well as also in the structure 13 according to FIG. 2b, to select highly different dimensions in the realization of the discrete microchambers, however, the following dimensions have proven to be for example suitable:

| | |
|---|---|
| Diameter of the silicon disk: | appr. 10–20 cm; |
| Thickness of the silicon disk: | 0.3–1 mm; |
| Thickness of agarose layer: | <10 μ; |
| Inner diameter of the microchambers 11 [sic], preferably implemented circularly: | appr. 0.5–5 mm; |
| Wall thickness of honeycomb structure between discrete chambers: | appr. 0.2 mm; |
| Height of walls of honeycomb structure: | appr. 0.1–2 mm; |
| Diameter of palladium island: | appr. 0.3 mm; |
| Thickness of polymer cover layer or semipermeable membrane, comprising for example Teflon: | <10 μ. |

In FIG. 2c is again shown schematically a detail in cross section of a further possible embodiment variant of an arrangement 14 according to the invention, provided for example for carrying out measurements, for observation or for analytical measuring methods through the bottom of the container 11. The structure comprises again a silicon quartz disk 8, a metal foil 4 as well as a membrane 5 disposed on the bottom of the container 11. The structure is covered by a magnet disk 9 which simultaneously forms the cover of the container or of the special steel box 11.

Figure 2C:
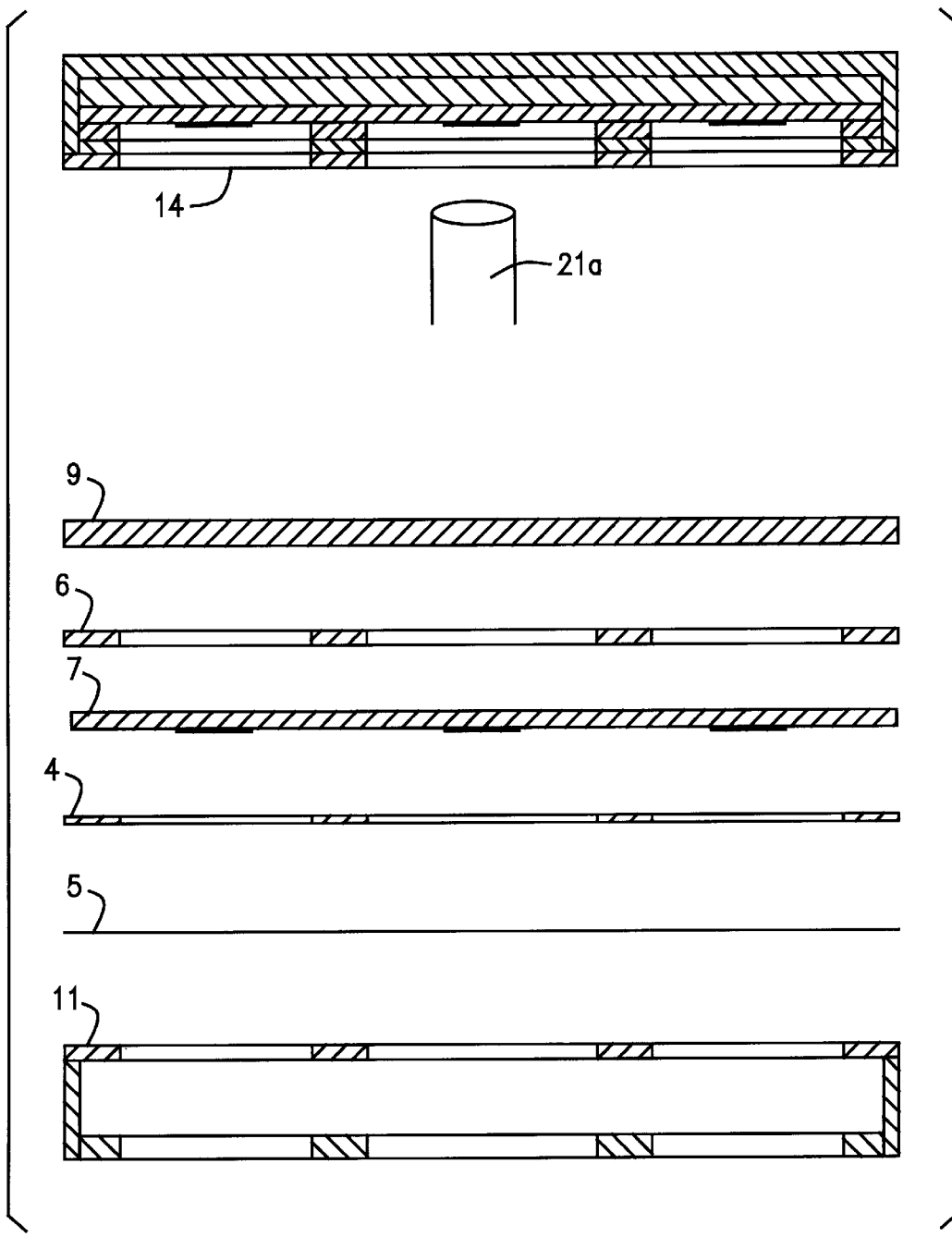

The compact cell culture arrangements or structures 12 to 14, depicted according to the invention, comprising the chamber structures described in detail in FIGS. 2a to 2c, are especially suitable for the investigations of tumors containing a multiplicity of different cells. Therein, first the cell mass of a tumor sample (biopsy) is divided, dispersed into single cells. Practice has shown that it is necessary to investigate a relatively large number of these single cells. Such sample comprises as a rule approximately 100,000 to 1,000,000 single cells, which is why it is desirable to study at least several 1,000 of a discrete sample in order to obtain a significant view of the tumor biopsy. The separation and dispersion of such a cell biopsy is well known.

The individual cells, obtained through the cited dispersion, are now placed into the discrete, not yet closed, ponds 17. Lastly, the honeycomb structure is closed toward the outside by means of the semipermeable wall 5, and specifically toward the cited palladium island 18. After filling and closing chambers 17, as a rule, standardized low-molecular growth components or nutrients are added through the cover sheeting.

The advantage of the arrangement or structure described according to the invention lies therein that it comprises a multiplicity of compact, biologically sterile microlaboratories which offers the following feasibilities:

1. The implantation of any desired number of single cells to be cultured (from a sample of several 1000) into discrete self-contained chambers which can subsequently be observed and analyzed visually as well as with instruments.
2. Morphological or spectroscopic investigations of the cultures and the media enveloping them under optimum optical conditions by means of upright or inverted, conventional or confocal laser scanning microscopy.
3. The capability of adding standardized low-molecular medium components, such as buffer, nutrients or antibiotics.
4. Elimination of waste products, produced by the living and growing cell through the semipermeable wall.
5. Supplying the discrete chambers with respiratory or other gases, again through the semipermeable wall.
6. Continuous or temporary addition of low-molecular active substances such as pharmacological agents or toxic environmental factors.
7. Control of biochemical and, if relevant, of the microbiological environment individually for each culture at the time of the implantation or at any time by means of microinjection through the cover sheeting.
8. Jointly or differentiably influencing the nonchemical test modalities, such as ionizing or nonionizing radiation at any time by means of external exposure.
9. Joint or differentiable temperature control.
10. Sterile conditions for the cultures during the storage, transport, handling, during the analyses and the observation in nonsterile environments.

In FIGS. 2a to 2c is shown schematically a microscope or other optical device 21 or 21a in order to demonstrate the way in which cells in a discrete chamber can be observed or analyzed during the investigation. It was found for example that healthy cells form so-called "monolayers" which can be observed in simple manner with conventional microscopy while so-called transformed cells ("tumor cells") can form a "multilayer" structure which can be observed or analyzed better by means of a confocal microscope.

The realization of the compact cell culture plate defined according to the invention is based on a novel construction principle of cell culture microchambers and the configuration of such chambers with which limited as well as also large-scale manual or automatic isolation, culture, characterization and archiving of individual living cells, cell populations or structured systems of cell, such as small multicellular organism or tumor or tissue explants, become possible.

The compact cell culture plate described according to the invention, constructed in the manner of a sandwich on simple disk-like components, entails enormous application and handling advantages. For one, it is relatively small and compact, and, for another, an extremely great multiplicity of information is stored on it, which can be analyzed or called up with high precision in an extremely simple way. For example, such cell culture plate or disk can be inserted analogously to a compact disk into an analytical device or processing device, and a specific cell chamber can be precisely analyzed or influenced specifically by means of precisely defined coordinates. In this way the many microlaboratories can be scanned relatively rapidly, in any desired way or systematically, for example, by the stepwise radial and azimuthal movement of the disk.

A multiplicity of applications is evident for the compact cell culture plate claimed according to the invention, such as for example in molecular or cellular genetics, in microbiology, in tumor biology, toxicology, pharmacology and radiobiology. The "compact cell culture disk" (CCCD) is suitable for automated routine applications in biotechnology, clinical medicine or environmental technology and is applied, for example, in the field of teaching. The strongly increased capacity, precision, reproducibility and asepsis permits specifically in manual as well as also computer-controlled processes carrying out so-called "cell cloning", i.e. isolation, culture, characterization and archiving of individual clones.

Figure 3A:
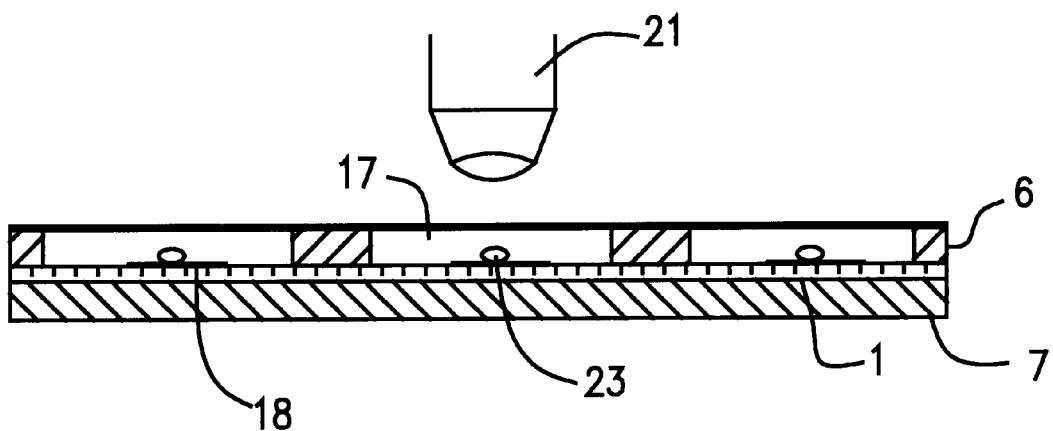
Figure 3B:
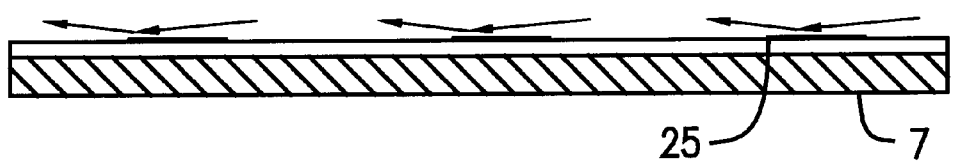

In FIGS. 3a and 3b are schematically indicated two possible measuring or analytical methods according to which the cell or cell cultures to be cultured or having been cultured can be observed or analyzed. FIG. 3a shows schematically in cross section an arrangement 1 according to the invention with the microchambers or laboratories 17 accessible for measurements from above. The observation or analysis of the discrete cell spots 23 consequently takes place in situ during the culture process, for example by means of an optical device 21, and it is understood that other analytical devices can also be used. This measuring method is advantageously applicable during the culture process since it can be repeated any number of times. The entire compact cell culture plate or disk 1 is therein scanned in order to scan a specific selection or all chambers 17 provided in the arrangement. In FIG. 3b, in contrast, for conclusive highly precise measurement or for the clearing of the material, the entire covering of the original structure has been removed and the cell cultures or the cultured biosamples are present in the form of dead, fixed, optionally freeze-dried or incinerated material 25. Measurement or analysis of the killed material takes place by means of photon or neutron radiation incident in the direction of the indicated arrow. The great advantage of this measuring method lies therein that it provides, on the one hand, highly precise results and, on the other hand, due to the nearly parallel impingement of the rays on the material to be investigated, no scattering onto the subjacent base, such as for example the silicon disk, takes place. Measurements by means of photons of other particle radiation or X-ray radiation or thermal neutrons is well known within prior art.

Figure 4A:
Figure 4B:
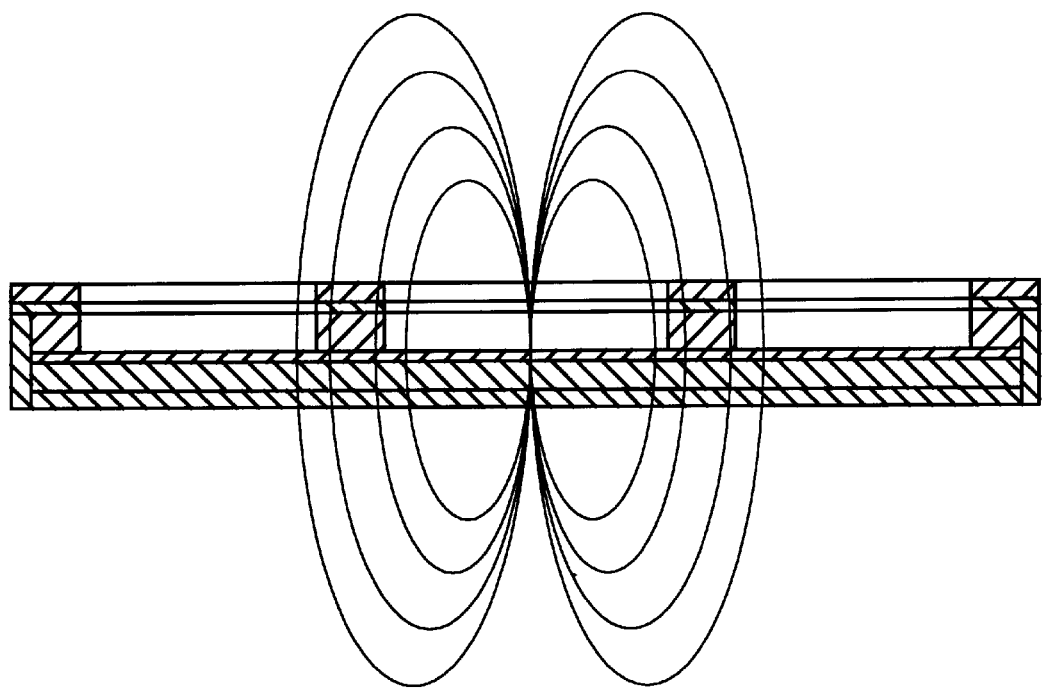

In contrast to the microchamber structures or arrangements 12 to 14 depicted sectionally in FIGS. 2a to 2c, which are held together in the form of a sandwich by means of magnetic forces, it is understood that it is also possible to produce such arrangements or structures in conventional ways by means of affixing them by adhesion. This is in particular necessary whenever, as shown in section and schematically in FIG. 4b, the magnetic fields occurring therein are perceived as a disturbance to the culture of cells. It can potentially also be of disadvantage if the sandwich structure is held together by means of magnetic fields and the requirement potentially exists for that reason of producing a compact cell culture plate or an arrangement or structure according to the invention, as shown schematically in FIG. 4a, i.e. without any magnetic fields being present at all. Such compact cell culture plate according to the invention can preferably be produced according to the process steps described in the following:

1. Creation of the honeycomb-like structure or matrix 6 of a relatively rigid material, such as for example polycarbonate, silicon, ceramic or Teflon-coated nickel with preferably circular perforations which are provided for the formation of the microchambers 17. High packing density is preferably selected therein so that on minimum space the largest possible number of microchambers 17 can be formed.

2. This grid- or honeycomb-like structure or matrix is affixed by adhesion on a thin polymer film 5 (membrane), for example comprising Teflon or polystyrene, and as the substance for adhesion, a silicone derivative or a UV-curing polymer can be used for example. The polymer film forms the above described, preferably semipermeable, covering 5 of desired constitution of the discrete chambers 17.

3. Filling of the discrete ponds 17 with nutrient fluids, sera, active agents etc.

4. Placing the individual cells 13 into the chambers open toward the top.

5. Onto a silicon wafer or a glass plate, for example having a diameter of approximately 10 cm, initially a thin polymer layer, for example comprising agarose, is placed. In agreement with the honeycomb structure, on the silicon wafer or on the agarose layer the palladium islands or other structures can be applied or placed.

6. The silicon wafer produced in this way is placed onto the above cited honeycomb structure, and the honeycomb structure as well as the silicon wafer comprise a marking or a notch 19 (FIG. 1) so that the silicon wafer is placed congruently onto the honeycomb structure. The affixing by adhesion of the silicon wafer with the honeycomb structure takes place for example by means of aliphatic silicone.

7. Lastly, the arrangement or compact cell culture plate according to the invention produced in this way is rotated by 180° into the position according to FIG. 3 so that the silicon wafer serves as a base or support.

Alternatively, the possibility exists that, instead of affixing, on the one hand, synthetic material film with the honeycomb-like structure with the silicon disk, by adhesion, the magnets already cited are used. For this purpose during the production of the honeycomb structure, still open on one side, according to FIG. 2 the polymer film, forming the semipermeable wall, is placed onto a grid-like nickel or special steel foil, which, in agreement with the honeycomb perforations also comprises perforations. Again, it can be ensured through a lateral notch 19 in the metal foil and the polycarbonate honeycomb structure that the discrete chambers 17 are visible through the nickel or metal foil, for example for the purposes of analysis. After applying the silicon disk 7 onto the rear side of the silicon disk, a magnet plate 9 is emplaced such that the arrangement or compact cell culture sandwich structure formed in this way is held together by means of magnetic forces. Lastly, again the compact cell culture plate formed in this way is rotated by 180° whereby the discrete chambers 17 become visible through the perforations in the foil for the purposes of analysis or processing. Alternatively or in addition to the magnetic foil it is also possible to produce the honeycomb-like structure, instead of a polymer, for example of nickel or another magnetic material.

Figure 5A:
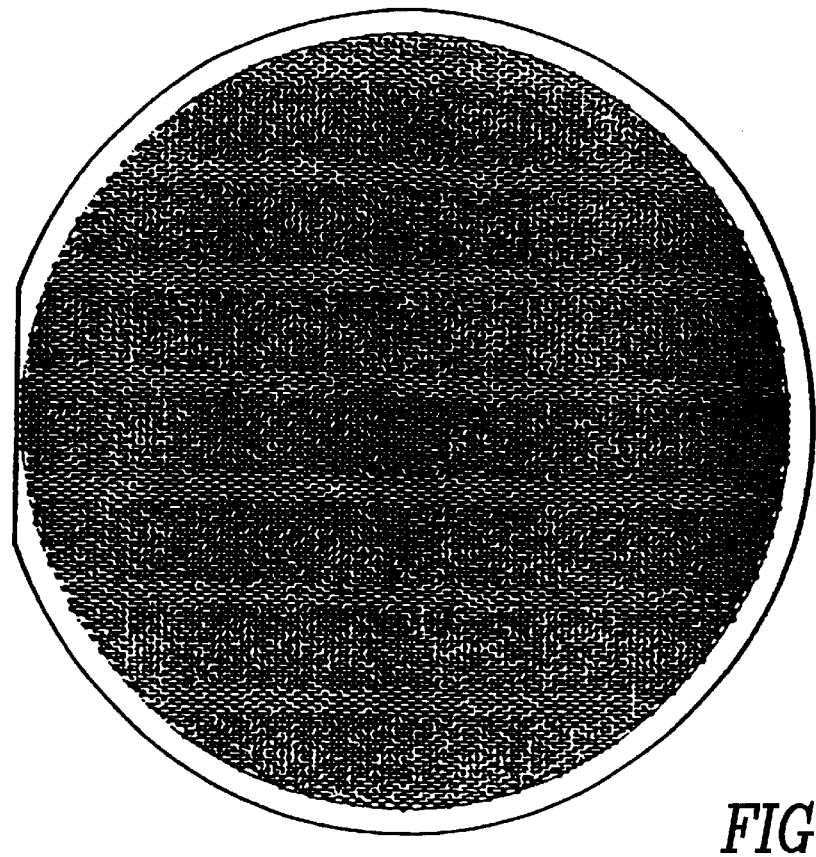

In FIG. 5a a further example of a so-called "compact cell culture disk" is shown wherein, with the exception of a relatively narrow margin portion, the entire plate is provided with the honeycomb-like structure or with discrete microchambers. In this way it becomes, for example, possible to dispose more than 8000 microchambers on a disk having a diameter of 10 cm and discrete microchambers having a diameter of 0.8 mm.

Figure 5B:
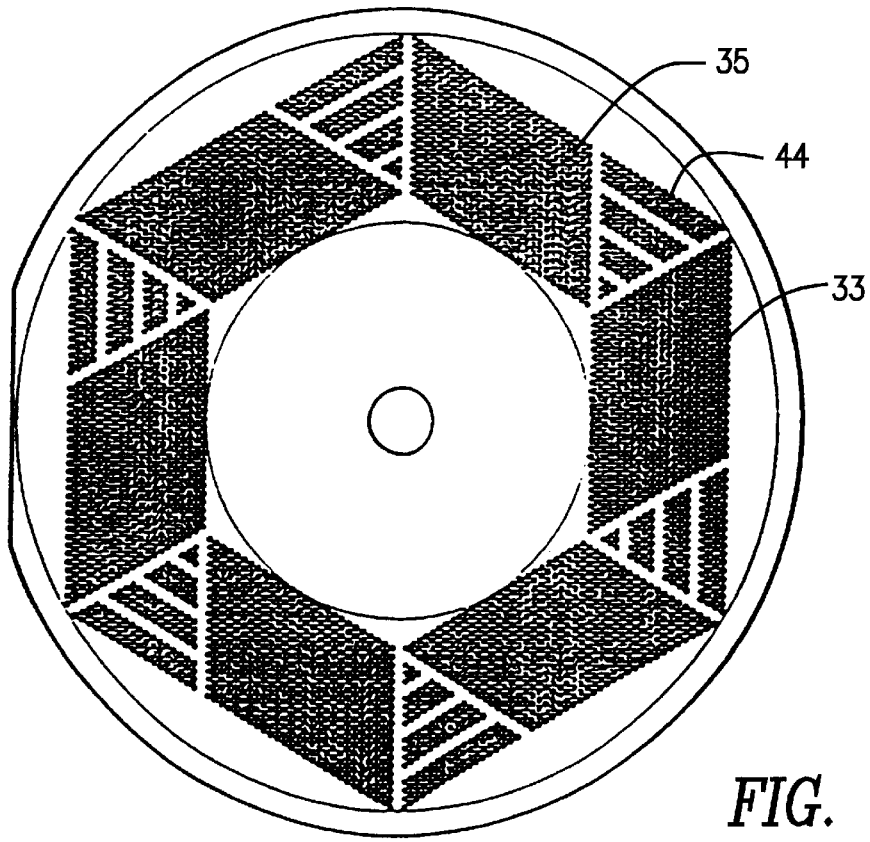

FIG. 5b shows, in turn, a further embodiment according to the invention of a "compact cell culture disk", in particular suitable for storing, culturing and analyzing cells or cell cultures or other biosamples of different test series. It is for example possible to add cells from a first sample to the region of structure 33 while cells from a second sample have to be added to the discrete chamber or ponds of the structure or the region 35, etc. In the intermediate regions 34 or 44 disposed between these main regions it is possible to place reference cells but it is also possible to culture and observe cells for the culture of which only a relatively small number is necessary.

Figure 6:
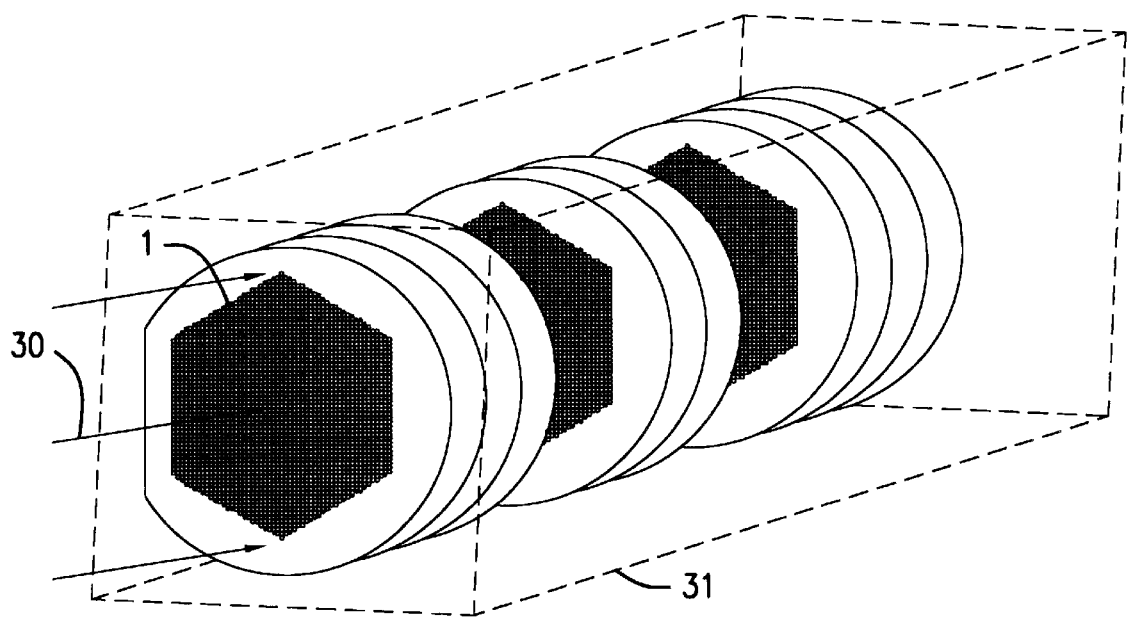

In FIG. 6 lastly an application of the arrangements described according to the invention is shown, in particular suitable in radiation research and radiation medicine. Into a model structure 31, for example filled with water, are placed the discrete compact cell culture disks 1 produced according to the invention, as shown in FIG. 6. It is now possible to investigate the biological effectiveness as is function of the coordinates of the various sample systems or samples on the different compact cell culture disks. This takes place thereby that the model structure 31, comprising the compact cell culture disks, is exposed to electromagnetic fields, X-ray, proton, neutron or any other radiation 30. Depending on where in the system of coordinates of the model structure 31 a discrete microchamber 17 is disposed, a different exposure to the waves conducted through the structure 31 results.

It is understood that the cell culture arrangements, i. e. "compact cell culture disks" depicted in FIGS. 1 to 6 and defined according to the invention are only examples which can be changed, modified and supplemented in any desired way. It is in particular also possible to use, instead of the cited dimensions, other dimensions and, instead of the materials used, other suitable materials. Thus it is for example also possible to use, instead of palladium, another suitable inert metal, other organic substances or chemically fixed ligands. Instead of polycarbonate, another suitable, preferably transparent, hydrophobic polymer, a metal, a semiconductor or insulating material can be used. As the semipermeable cover layer can also be used, instead of Teflon or polystyrene, other materials such as are used generally for the production of fully permeable, semipermeable or non-permeable walls. The use of agarose on the silicon wafer is in particular suitable since agarose is inert and is avoided by cells during their growth. But it is also understood that it is possible to use for the coating of the silicon wafer other materials which have suitable properties. Lastly, instead of the silicon disk, a transparent disk can be used (quartz or another glass) or again a disk comprising, for example, polycarbonate or another polymer which has a low absorption of water, is thermally stable, dimensionally stable and has high impact strength. Various composite material structure are also relevant, such as for example a honeycomb structure of silicon with provided perforations which is equipped with quartz windows.

With respect to the possible application of the arrangement defined according to the invention also no restrictions exist. In addition to the described application feasibilities it is in particular also possible to use such compact cell structure disks in aeronautics. It is for example possible to subject cells or cell cultures, disposed on a compact cell culture disk defined according to the invention, to space conditions in order to study in this way, for example, effects of zero gravity conditions, of cosmic radiation, etc. on the individual cells during their culture.

It is essential that in the selection of the various materials an arrangement for the culture of cells can be obtained whereby it is feasible to dispose a multiplicity of microchambers on a base, which can be separated one from the other, are closed by a preferably semipermeable wall against the environment, and can be observed through suitable window openings.

I claim:

1. Arrangement for culturing biosamples, comprising:

a planar, at least nearly smooth base;

a grid matrix having a multiplicity of perforations therethrough, the perforations lying in a regular pattern and defining sidewalls of a multiplicity of separate microchambers, the matrix resting on and being connected to the base;

a semipermeable membrane extending over and being in contact with the matrix for defining a cover for the microchambers and for separating the microchambers from the environment, the microchambers each being closed by a sandwich structure formed by the base, the matrix and the membrane.

2. Arrangement as claimed in claim 1, wherein the base is formed by a thin plane-parallel, disk of optically high and uniform quality.

3. Arrangement as claimed in claim 1, wherein the microchambers are circular, with a diameter of approximately 0.2 to 5 mm and at least a portion of the microchambers being disposed in a honeycomb pattern.

4. Arrangement as claimed in claim 1, wherein the base is covered by a transparent gel or polymer layer lacking cell affinity, on which the microchambers are disposed.

5. Arrangement as claimed in claim 1, wherein on a bottom of each the microchamber, resting on the base, one spot each implemented in the form of an island, comprising a thin layer suitable for the culture of cells is disposed.

6. Arrangement as claimed in claim 1, wherein the matrix comprises a rigid and dimensionally stable material, selected from the group consisting of polycarbonate, silicon, a metallic material, ceramic and a composite material.

7. Arrangement as claimed in claim 1, wherein the membrane comprises a polymer material, selected from the group consisting of Teflon, polystyrene and polycarbonate, with selective permeability.

8. Arrangement as claimed in claim 1, wherein the base is circular and has a diameter of approximately 5 to 20 cm with a central perforation, in order to dispose the base on a holder of a microscope, measuring device or working device.

9. Arrangement as claimed in claim 1, wherein the arrangement is disposed in a container with openings transparent to light on at least one side in order to carry out measurements with the arrangement disposed in the container.

10. Arrangement as claimed in claim 1, wherein a regular pattern of perforations of the grid matrix comprises a honeycomb pattern.

11. Arrangement as claimed in claim 1, including magnet means for holding the sandwich structure together.

12. Arrangement as claimed in claim 11, wherein the magnet means comprises a magnet on one side of the base opposite from the matrix and a magnetically attractable film over the membrane being attracted by the magnet.

13. Process for producing an arrangement for culturing biosamples, comprising:

forming a grid matrix structure comprising perforations defining open culturing spaces for biosamples;

applying and connecting the grid matrix structure to a semipermeable membrane acting as a covering layer;

placing into the spaces, closed in the downward direction by the semipermeable membrane, nutrients and cells; and applying a disk plate as a base in order to close the perforations opposite to the semipermeable membrane.

14. Process as claimed in claim 13, wherein the semipermeable membrane is fixedly connected with the grid matrix structure by means of a silicon derivative or a UV-curing material.

15. Process as claimed in claim 13, wherein the disk base is fabricated of silicon, quartz or glass, subsequently coated by means of a transparent gel or polymer layer lacking cell affinity, thereafter providing the layer with spots having cell affinity in the form of islands geometrically congruent with the perforations of the grid matrix structure, and connecting the base congruently with the grid matrix structure such that each spot comes to lie substantially centrally in a perforation.

16. Process as claimed in claim 13, wherein the base and the structure are fixedly connected one with the other by means of a aliphatic substance.

17. Process as claimed in claim 13, wherein the membrane is placed onto a metal plate provided with perforations, with the perforations corresponding geometrically to the perforations of the grid matrix structure, and subsequent to applying the grid matrix structure to the base, applying a magnet to the base, opposite to the grid matrix structure to hold together the membrane, grid matrix structure and base due to the attraction of the metal plate through the magnet.

* * * * *